(12) United States Patent
Gladwin et al.

(10) Patent No.: US 10,980,864 B2
(45) Date of Patent: Apr. 20, 2021

(54) USE OF MICROPEROXIDASES FOR THE TREATMENT OF CARBOXYHEMOGLOBINEMIA

(71) Applicant: University of Pittsburgh—Of the Commonwealth System of Higher Education, Pittsburgh, PA (US)

(72) Inventors: Mark Thomas Gladwin, Pittsburgh, PA (US); Jesus Tejero Bravo, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/313,231

(22) PCT Filed: May 19, 2015

(86) PCT No.: PCT/US2015/031483
§ 371 (c)(1),
(2) Date: Nov. 22, 2016

(87) PCT Pub. No.: WO2015/179344
PCT Pub. Date: Nov. 26, 2015

(65) Prior Publication Data
US 2017/0189495 A1    Jul. 6, 2017

Related U.S. Application Data (60) Provisional application No. 62/001,754, filed on May 22, 2014.

(51) Int. Cl.
| | | |
|---|---|---|
| *A61K 38/44* | (2006.01) | |
| *A61K 38/41* | (2006.01) | |
| *A61K 9/00* | (2006.01) | |
| *A61P 7/00* | (2006.01) | |

(52) U.S. Cl.
CPC ............ *A61K 38/44* (2013.01); *A61K 9/0019* (2013.01); *A61K 38/415* (2013.01); *A61P 7/00* (2018.01); *C12Y 109/03001* (2013.01); *C12Y 111/01007* (2013.01)

(58) Field of Classification Search
CPC .... A61K 38/44; A61K 9/0019; A61K 38/415; C12Y 109/03001; C12Y 111/01007; A61P 7/00
See application file for complete search history.

(56) References Cited

U.S. PATENT DOCUMENTS

| | | | |
|---|---|---|---|
| 5,525,630 A | 6/1996 | Hoffman | |
| 6,013,623 A | 1/2000 | Spector et al. | |
| 2009/0024105 A1 | 1/2009 | Levy et al. | |
| 2011/0256567 A1* | 10/2011 | Berthelot et al. | 435/23 |
| 2011/0312914 A1 | 12/2011 | Kano et al. | |

FOREIGN PATENT DOCUMENTS

| | | |
|---|---|---|
| EP | 0497794 | 7/1994 |
| WO | WO 1991/005858 | 5/1991 |
| WO | WO 2001/022960 | 4/2001 |

OTHER PUBLICATIONS

Everse J. et al., "Physical and catalytic properties of a peroxidase derived from cytochrome c", Biochemica et Biophysica Acta, 2011, vol. 1812, pp. 1138-1145 (Year 2011).*
Larsen R. et al., "Hemecytotoxicity and the pathogenesis of immune-mediated inflammatory diseases", Frontiers in Pharmacology, a Review article, May 2012, vol. 3, article 77, pp. 1-17 (Year 2012).*
Feder N. "Microperoxidase: An ultrastructural tracer of low molecular weight", The Journal of Cell Biology, 1971, vol. 51, pp. 339-343 (Year 1971).*
Kao L. W. et al—"Carbon monoxide poisoning", Medical Clinics of North America, 2005, vol. 89, pp. 1161-1194 (Year: 2005).*
Braun and Thöny-Meyer, "Biosynthesis of Artificial Microperoxidases by Exploiting the Secretion and Cytochrome C Maturation Apparatuses of *Escherichia coli*," *Proc. Natl. Acad. Sci. USA*, vol. 101:12830-12835, 2004.
Kitagishi et al., "A Diatomic Molecule Receptor that Removes CO in a Living Organism," *Angew. Chem. Int. Ed.*, vol. 49:1312-1315, 2010.
Product Information sheet for Microperoxidase (MP-11) sodium salt, available on the World Wide Web at sigmaaldrich.com/content/dam/sigma-aldrich/docs/Sigma/Product_Information_Sheet/1/m6756pis.pdf, 1 page, created Jun. 15, 2007.
Samaja et al., The Dissociation of Carbon Monoxide from the Alpha and the Beta Subunits of Human Carbonmonoxy Hemoglobin, *Biochem. Biophys. Res. Comm.*, vol. 148:1196-1201, 1987.
Sharma et al., "Dissociation of CO from Carboxyhemoglobin," *J. Biol. Chem.*, vol. 251:4267-7272, 1976.
Spee et al., "The Influence of the Peptide Chain on the Kinetics and Stability of Microperoxidases," *Eur. J. Biochem.*, vol. 241:215-220, 1996.
Geckeler, "Advanced Macromolecular and Supramolecular Materials and Processes," Springer, New York, pp. 1, 2 and 182, Jan. 1, 2003.

(Continued)

*Primary Examiner* — Satyendra K Singh
(74) *Attorney, Agent, or Firm* — Klarquist Sparkman, LLP (57) ABSTRACT

It is disclosed herein that microperoxidases are capable of binding carbon monoxide (CO) with high affinity and displacing CO from hemoglobin, thereby acting as CO scavengers. The present disclosure provides methods of treating carboxyhemoglobinemia (or CO poisoning) in a subject by administering a therapeutically amount of an isolated or recombinant microperoxidase. Methods of removing CO from hemoglobin in blood or tissue by administering a therapeutically amount of an isolated or recombinant microperoxidase are also described. Methods of determining the effectiveness of a microperoxidase for removing CO from hemoglobin are further described.

11 Claims, 3 Drawing Sheets
Specification includes a Sequence Listing.

(56) References Cited

OTHER PUBLICATIONS

Mondelli et al., "3D structure of microperoxidase-11 by NMR and molecular dynamic studies," *Magn Reson Chem* 38:229-240, 2000.
Supplementary European Search Report issued in connection with EP Application No. 15796824.9 dated Feb. 5, 2018 (6 pages).
Koida et al., "Carbon Monoxide (CO)-Induced Hypoxia in Mice: Evaluation as an Experimental Model of Cerebral Ischemia for Drug Screening," *Japan J Pharmacol* 51:273-278, 1989.
Penney, "Acute carbon monoxide poisoning: animal models: A review," *Toxicology* 62:123-160, 1990.
Thom, "Carbon monoxide-mediated brain lipid peroxidation in the rat," *J Appl Physiol* 68(3):997-1003, 1985.
Azarov et al., "Five-coordinate H64Q neuroglobin as a ligand-trap antidote for carbon monoxide poisoning," *Sci Transl Med* 8(368): 368ra173, 2016.
O'Malley and O'Malley, "Carbon Monoxide Poisoning," Merck Manual, available online at https://www.merckmanuals.com/professional/injuries-poisoning/poisoning/carbon-monoxide-poisoning (3 pages), 2018.
Smulevich et al., "Raman and Infrared Spectra of Cytochrome C Peroxidase-Carbon Monoxide Adducts in Alternative Conformational States," *Biochemistry* 25(15):4426-4430, 1986.
Marques et al., "Hemepeptide Models for Hemoproteins: The Behavior of N-acetylmicroperoxidase-11 in Aqueous Solution," *J. Inorg. Biochem.*, vol. 75:281-291, 1999.
Marques, "Insights into Porphyrin Chemistry provided by the Microperoxidases, the Haempeptides Derived from Cytochrome c," *Dalton Trans.*, vol. 39:4371-4385, 2007.
Mondelli et al., "3D Structure of Microperoxidase-11 by NMR and Molecular Dynamic Studies," *Magn. Reson. Chem.*, vol. 38:229-240, 2000.
Spector et al., "Investigation of the Mechanism of Action of Microperoxidase-11, (MP11), a Potential Anti-cataract Agent, with Hydrogen Peroxide and Ascorbate," *Exp. Eye Res.*, vol. 71:183-194, 2000.

\* cited by examiner

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa = any natural or non-canonical amino acid

<400> SEQUENCE: 1

Cys Xaa Xaa Cys His
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = any natural or non-canonical amino acid
<220> FEATURE:
<221> NAME/KEY: MISC_FEATURE
<222> LOCATION: (3)..(4)
<223> OTHER INFORMATION: Xaa = any natural or non-canonical amino acid

<400> SEQUENCE: 2

Xaa Cys Xaa Xaa Cys His
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = any natural or non-canonical amino acid
<220> FEATURE:
<221> NAME/KEY: MISC_FEATURE
```

```
<222> LOCATION: (3)..(4)
<223> OTHER INFORMATION: Xaa = any natural or non-canonical amino acid
<220> FEATURE:
<221> NAME/KEY: MISC_FEATURE
<222> LOCATION: (7)..(7)
<223> OTHER INFORMATION: Xaa = any natural or non-canonical amino acid

<400> SEQUENCE: 3

Xaa Cys Xaa Xaa Cys His Xaa
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Val Gln Lys Cys Ala Gln Cys His Thr Val Glu
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Cys Ala Gln Cys His Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Cys Ala Gln Cys His Thr Val Glu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Lys Cys Ala Gln Cys His Thr Val Glu
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Cys Lys Ala Cys His Met Val Gln Ala Pro Asp Gly Thr Asp Ile Val
1               5                   10                  15

Lys
```

```
<210> SEQ ID NO 9
<211> LENGTH: 21
<212> TYPE: PRT
<213> ORGANISM: Artificial Sequence
<220> FEATURE:
<223> OTHER INFORMATION: Synthetic peptide

<400> SEQUENCE: 9

Gly Asp Val Glu Lys Gly Lys Lys Ile Phe Ile Met Lys Cys Ser Gln
1               5                   10                  15

Cys His Thr Val Glu
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Gly Asp Val Glu Lys Gly Lys Lys Ile Phe Val Gln Lys Cys Ala Gln
1               5                   10                  15

Cys His Thr Val Glu
            20
```

USE OF MICROPEROXIDASES FOR THE TREATMENT OF CARBOXYHEMOGLOBINEMIA

CROSS REFERENCE TO RELATED APPLICATIONS

This is the U.S. National Stage of International Application No. PCT/US2015/031483, filed May 19, 2015, published in English under PCT Article 21(2), which claims the benefit of U.S. Application No. 62/001,754, filed May 22, 2014, which is herein incorporated by reference in its entirety.

ACKNOWLEDGMENT OF GOVERNMENT SUPPORT

This invention was made with government support under grant number HL103455 awarded by the National Institutes of Health. The government has certain rights in the invention.

FIELD

This disclosure concerns microperoxidases that bind carbon monoxide with high affinity, and their use for the treatment of carboxyhemoglobinemia and carbon monoxide poisoning.

BACKGROUND

Inhalation exposure to carbon monoxide represents a major cause of environmental poisoning. Individuals can be exposed to carbon monoxide in the air under a variety of circumstances, such as house fires, use of generators or outdoor barbeque grills used inside the house, or during suicide attempts by running automobiles in closed spaces. Carbon monoxide binds to hemoglobin (producing carboxyhemoglobin) and to hemoproteins in cells, in particular, the enzymes of the respiratory transport chain. The accumulation of carbon monoxide bound to hemoglobin and other hemoproteins impairs oxygen delivery and oxygen utilization for oxidative phosphorylation. This ultimately results in severe hypoxic and ischemic injury to vital organs such as the brain and the heart. Individuals who accumulate greater than 15% carboxyhemoglobin in their blood are at risk for brain injury and neurocognitive dysfunction. Individuals with higher levels of carboxyhemoglobin are at risk for death. Patients with very high carboxyhemoglobin levels who survive typically suffer from irreversible brain injury and brain death.

Despite the availability of methods to rapidly diagnose carbon monoxide poisoning with standard arterial and venous blood gas analysis and co-oximetry, and despite an awareness of risk factors for carbon monoxide poisoning, there are no available antidotes for this toxic exposure. The current therapy is to give 100% oxygen by face mask, and when possible to expose patients to hyperbaric oxygen. The mechanism for hyperbaric oxygen therapy is the oxygen will increase the rate of release of the carbon monoxide from hemoglobin and from tissues and accelerate the natural clearance of carbon monoxide. However, this therapy has only a modest effect on carbon monoxide clearance rates and based on the complexity of hyperbaric oxygen facilities, this therapy is not available in the field.

SUMMARY

A need exists for an effective, rapid and readily available therapy to treat carboxyhemoglobinemia, also known as carbon monoxide poisoning. It is disclosed herein that microperoxidases are capable of binding carbon monoxide (CO) with high affinity and displacing CO from hemoglobin, thereby acting as CO scavengers. The data disclosed herein demonstrates that isolated or recombinant microperoxidases can be used, for example, in methods of removing carbon monoxide from hemoglobin in blood or animal tissue, and in methods of treating carboxyhemoglobinemia.

Provided herein is a method of treating carboxyhemoglobinemia in a subject by selecting a subject with carboxyhemoglobinemia and administering to the subject a therapeutically effective amount of an isolated or recombinant microperoxidase, wherein the microperoxidase comprises a peptide bound to a porphyrin moiety. In some embodiments, the amino acid sequence of the peptide comprises CXXCH (SEQ ID NO: 1), where X is any natural or non-canonical amino acid.

Further provided is a method of removing carbon monoxide from hemoglobin in blood or tissue by contacting the blood or tissue with an isolated or recombinant microperoxidase, wherein the isolated or recombinant microperoxidase comprises a peptide bound to a porphyrin moiety. In some embodiments, the amino acid sequence of the peptide comprises CXXCH (SEQ ID NO: 1), where X is any natural or non-canonical amino acid. In some examples, the method is an in vitro method. In other examples, the method is an in vivo method, wherein contacting the blood or tissue with an isolated or recombinant microperoxidase comprises administering the isolated or recombinant microperoxidase to a subject.

Also provided are methods of determining the effectiveness of an isolated or recombinant microperoxidase.

The foregoing and other objects, features, and advantages will become more apparent from the following detailed description, which proceeds with reference to the accompanying figures.

SEQUENCE LISTING

The amino acid sequences listed in the accompanying Sequence Listing are shown using standard three letter code for amino acids, as defined in 37 C.F.R. 1.822. The Sequence Listing is submitted as an ASCII text file, created on Nov.

15, 2016, 3.01 KB, which is incorporated by reference herein. In the accompanying sequence listing:

SEQ ID NO: 1 is an amino acid motif of a microperoxidase capable of binding a porphyrin moiety; in this sequence, Xaa is any natural or non-canonical amino acid.

SEQ ID NOs: 2 and 3 are representative amino acid consensus sequences of recombinant microperoxidases for use with the disclosed methods; in these sequences, Xaa is any natural or non-canonical amino acid.

SEQ ID NO: 4 is the amino acid sequence of the peptide portion of microperoxidase-11 (MP11).

SEQ ID NO: 5 is the amino acid sequence of the peptide portion of microperoxidase-6 (MP6).

SEQ ID NO: 6 is the amino acid sequence of the peptide portion of microperoxidase-8 (MP8).

SEQ ID NO: 7 is the amino acid sequence of the peptide portion of microperoxidase-9 (MP9).

SEQ ID NO: 8 is the amino acid sequence of the peptide portion of microperoxidase-17 (MP17).

SEQ ID NO: 9 is the amino acid sequence of a peptide derived from human cytochrome c.

SEQ ID NO: 10 is the amino acid sequence of a peptide derived from horse cytochrome c.

DETAILED DESCRIPTION

I. Abbreviations
  CO carbon monoxide
  Hb hemoglobin
  HbA hemoglobin A
  HbCO carboxyhemoglobin
  MP microperoxidase
  RBC red blood cell
  RBC-CO carbon monoxide-saturated red blood cells II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. a microperoxidase), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Antidote: An agent that neutralizes or counteracts the effects of a poison.

Carbon monoxide (CO): A colorless, odorless and tasteless gas that is toxic to humans and animals when encountered at sufficiently high concentrations. CO is also produced during normal animal metabolism at low levels.

Carboxyhemoglobin (HbCO): A stable complex of carbon monoxide (CO) and hemoglobin (Hb) that forms in red blood cells when CO is inhaled or produced during normal metabolism.

Carboxyhemoglobinemia or carbon monoxide poisoning: A condition resulting from the presence of excessive amounts of carbon monoxide in the blood. Typically, exposure to CO of 100 parts per million (ppm) or greater is sufficient to cause carboxyhemoglobinemia. Symptoms of mild acute CO poisoning include lightheadedness, confusion, headaches, vertigo, and flu-like effects; larger exposures can lead to significant toxicity of the central nervous system and heart, and even death. Following acute poisoning, long-term sequelae often occur. Carbon monoxide can also have severe effects on the fetus of a pregnant woman. Chronic exposure to low levels of carbon monoxide can lead to depression, confusion, and memory loss. Carbon monoxide mainly causes adverse effects in humans by combining with hemoglobin to form carboxyhemoglobin (HbCO) in the blood. This prevents oxygen binding to hemoglobin, reducing the oxygen-carrying capacity of the blood, leading to hypoxia. Additionally, myoglobin and mitochondrial cytochrome oxidase are thought to be adversely affected. Carboxyhemoglobin can revert to hemoglobin, but the recovery takes time because the HbCO complex is fairly stable. Current methods of treatment for CO poisoning including administering 100% oxygen or providing hyperbaric oxygen therapy.

Contacting: Placement in direct physical association; includes both in solid and liquid form. When used in the context of an in vivo method, "contacting" also includes administering.

Hemoglobin (Hb): The iron-containing oxygen-transport metalloprotein in the red blood cells of the blood in vertebrates and other animals. In humans, the hemoglobin molecule is an assembly of four globular protein subunits. Each subunit is composed of a protein chain tightly associated with a non-protein heme group. Each protein chain arranges into a set of alpha-helix structural segments connected together in a globin fold arrangement, so called because this arrangement is the same folding motif used in other heme/globin proteins. This folding pattern contains a pocket which strongly binds the heme group.

Heterologous: A heterologous protein or polypeptide refers to a protein or polypeptide derived from a different source or species.

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Metal ion: Any atomic element classified as a metal (such as a transition metal) having a net charge. In the context of the present disclosure, a metal ion of a porphyrin moiety typically (but not exclusively) has a net positive charge of 2+ or 3+. Exemplary metal ions include ferrous iron ($Fe^{2+}$) and ferric iron ($Fe^{3+}$).

Microperoxidase (MP): A small peptide, having two cysteine residues, that is covalently bound to a porphyrin moiety. Microperoxidases are obtained from cytochrome c proteolysis or through artificial synthesis.

Non-canonical amino acid: Any amino acid that is not one of the 20 standard amino acids found in nature and directly encoded by the genetic code. "Non-canonical" amino acids are also referred to as "non-standard" or "unnatural" amino acids.

Peptide or Polypeptide: A polymer in which the monomers are amino acid residues which are joined together through amide bonds. When the amino acids are alpha-amino acids, either the L-optical isomer or the D-optical isomer can be used, the L-isomers being preferred. The terms "peptide," "polypeptide" or "protein" as used herein are intended to encompass any amino acid sequence and include modified sequences, including modified globin proteins. The terms "peptide" and "polypeptide" are specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown in the following table.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamine or aspartic acid; or (d) a residue having a bulky side chain, for example, phenylalanine, is substituted for (or by) one not having a side chain, for example, glycine.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein. In general, the nature of the carrier will depend on the particular mode of administration being employed. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Porphyrin: An organic compound containing four pyrrole rings, functioning as a metal-binding cofactor in hemoglobin, chlorophyll and certain enzymes.

Protoporphyrin: A metal-free porphyrin. Protoporphyrins are tetrapyrroles containing the following side chains—methyl (4), propionic acid (2) and vinyl (2). Protoporphyrins combine, for example, with ferrous iron to form the heme group in hemoglobin and myoglobin, and with ferric iron to form the hemin group in catalase and some cytochromes.

Protoporphyrin IX: A precursor to prosthetic groups such as heme and cytochrome c. Protoporphyrin IX combines with ferrous iron ($Fe^{2+}$) to form the heme of hemoglobin.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered by addition, substitution, or deletion of a portion of a natural nucleic acid molecule or protein.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular organisms, including vertebrate organisms, a category that includes both human and non-human mammals.

Synthetic: Produced by artificial means in a laboratory, for example a synthetic polypeptide can be chemically synthesized in a laboratory.

Therapeutically effective amount: A quantity of compound or composition, for instance, an isolated or recombinant microperoxidase, sufficient to achieve a desired effect in a subject being treated. For instance, this can be the amount necessary to scavenge carbon monoxide in the blood or tissues, reduce the level of HbCO in the blood, and/or reduce one or more signs or symptoms associated with carbon monoxide poisoning.

Transition metal: An element whose atom has a partially filled d sub-shell, or which can give rise to cations with an incomplete d sub-shell. Transition metals are listed in the d-block of the periodic table. Transition metals include, for example, iron, cobalt, nickel, copper, zinc, palladium, silver, cadmium, scandium, titanium, vanadium, chromium, manganese, yttrium, zirconium, niobium, molybdenum, technetium, ruthenium, rhodium, hafnium, tantalum, tungsten, rhenium, osmium, iridium, platinum, gold, mercury, rutherfordium, dubnium, seaborgium, bohrium, hassium and meitnerium.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Detailed Description

A need exists for an effective, rapid and readily available therapy to treat carboxyhemoglobinemia (including CO poisoning). It is disclosed herein that microperoxidases are capable of binding CO with high affinity and displacing CO from hemoglobin, thereby acting as CO scavengers. The methods disclosed herein involve the use of isolated or recombinant microperoxidases for removing carbon monoxide from hemoglobin in blood or tissue, and for treating carboxyhemoglobinemia (or CO poisoning).

A. Methods of Treating Carboxyhemoglobinemia or CO Poisoning

Provided herein is a method of treating carboxyhemoglobinemia in a subject, comprising selecting a subject with carboxyhemoglobinemia and administering to the subject a therapeutically effective amount of an isolated or recombinant microperoxidase, wherein the isolated or recombinant microperoxidase comprises a peptide bound (such as covalently bound) to a porphyrin moiety. The peptides can be linear or cyclic.

In some embodiments, the amino acid sequence of the peptide comprises CXXCH (SEQ ID NO: 1), where X is any natural or non-canonical amino acid. In some examples, the amino acid sequence of the peptide comprises $X_{(1-20)}$ CXXCH (SEQ ID NO: 2) or $X_{(1-20)}$CXXCH$X_{(1-20)}$ (SEQ ID NO: 3), where X is any natural or non-canonical amino acid.

In particular non-limiting examples, the amino acid sequence of the peptide comprises VQKCAQCHTVE (SEQ ID NO: 4), which is the sequence of the MP11 peptide. In one example, the amino acid sequence of the peptide consists of VQKCAQCHTVE (SEQ ID NO: 4). In other examples, the amino acid sequence of the peptide comprises or consists of CAQCHT (SEQ ID NO: 5), CAQCHTVE (SEQ ID NO: 6), KCAQCHTVE (SEQ ID NO: 7), CKACHMVQAPDGTDIVK (SEQ ID NO: 8), GDVEKGKKIFIMKCSQCHTVE (SEQ ID NO: 9) or GDVEKGKKIFVQKCAQCHTVE (SEQ ID NO: 10). In yet other examples, the amino acid sequence of the peptide comprises any one of SEQ ID NOs: 4-10 with 1, 2, 3, 4 or 5 amino acid substitutions.

The porphyrin moiety of the microperoxidase comprises a metal ion. In some embodiments, the metal is a transition metal. In some examples, the transition metal is iron, zinc, palladium, manganese, cobalt, copper, nickel or cadmium. In one non-limiting example, the transition metal is iron. For example, in some instances, the metal iron is ferrous iron ($Fe^{2+}$).

In some embodiments, the porphyrin moiety comprises protoporphyrin IX. In some examples, protoporphyrin IX comprises an iron ion, such as $Fe^{2+}$. In other examples, iron is replaced with another transition metal, such as, but not limited to, zinc, palladium, manganese, cobalt, copper, nickel or cadmium.

In some instances, the amino acid composition of the peptide and/or the transition metal ion of the porphyrin moiety are selected to alter one or more properties of the microperoxidase. For example, modifications to the amino acid sequence and/or metal ion can be made to decrease peroxidase activity, to increase hydrophobicity or hydrophilicity (to increase plasma half-life or bioavailability), and/or to stabilize heme binding. In addition, particular amino acids may be selected in order to permit generation of a cyclic peptide.

In some embodiments, the subject has at least 3%, at least 5%, at least 10%, at least 15%, at least 20%, at least 30%, at least 40% or at least 50% carboxyhemoglobin (HbCO) in their blood (relative to total hemoglobin). Methods for measuring HbCO, such as by spectrophotometric or chromatographic methods, are well known in the art (see, e.g., U.S. Application Publication No. 2003/0202170; Rodkey et al., *Clin Chem* 25 (8):1388-1393, 1979; Barker et al., *Anesthesiology* 105 (5):892-897, 2006).

In some embodiments, the isolated or recombinant microperoxidase is administered by intravenous infusion.

In some embodiments, the microperoxidase is administered to a subject at a dose of about 1 gram to about 300 grams, such as about 10 grams to about 100 grams, about 10 grams to about 50 grams, about 30 grams to about 300 grams, or about 30 grams to about 150 grams. In particular examples, the microperoxidase is administered to a subject at a dose of about 1, about 10, about 20, about 30, about 40, about 50, about 60, about 70, about 80, about 90, about 100, about 125, about 150, about 175, about 200, about 225, about 250 or about 300 grams.

The isolated or recombinant microperoxidase can be administered to a subject in a single dose, or in multiple doses as needed, to reduce HbCO to a non-toxic level.

In some embodiments, the dose administered to the subject is the amount of isolated or recombinant microperoxidase required to decrease HbCO by at least 1%, at least 2%, at least 3%, at least 4%, at least 5%, at least 10%, at least 15%, at least 20%, at least 25%, at least 30%, at least 40%, at least 50%, at least 60%, at least 70%, at least 80% or at least 90% (compared to the level of HbCO before treatment) in blood and/or tissue of the subject.

B. Methods of Removing Carbon Monoxide from Hemoglobin

Also provided is a method of removing carbon monoxide from hemoglobin in blood or animal tissue, comprising contacting the blood or tissue with an isolated or recombinant microperoxidase, wherein the isolated or recombinant microperoxidase comprises a peptide covalently bound to a porphyrin moiety. Further provided is a method of reducing carboxyhemoglobin (HbCO) in blood or animal tissue, comprising contacting the blood or tissue with an isolated or recombinant microperoxidase, wherein the isolated or recombinant microperoxidase comprises a peptide covalently bound to a porphyrin moiety. The peptides can be linear or cyclic. Methods of making cyclic peptides are well known in the art (see, e.g., U.S. Patent Application Publication Nos. 2013/0310265; 2012/0122799; and 2011/0256567).

In some embodiments of the methods, the amino acid sequence of the peptide comprises CXXCH (SEQ ID NO: 1), where X is any natural or non-canonical amino acid. In some examples, the amino acid sequence of the peptide comprises $X_{(1-20)}$CXXCH (SEQ ID NO: 2) or $X_{(1-20)}$CXXCH$X_{(1-20)}$ (SEQ ID NO: 3), where X is any natural or non-canonical amino acid. In particular non-limiting examples, the amino acid sequence of the peptide comprises VQKCAQCHTVE (SEQ ID NO: 4), which is the sequence of microperoxidase-11 (MP11). In one example, the amino acid sequence of the peptide consists of VQKCAQCHTVE (SEQ ID NO: 4). In other examples, the amino acid sequence of the peptide comprises or consists of CAQCHT (SEQ ID NO: 5), CAQCHTVE (SEQ ID NO: 6), KCAQCHTVE (SEQ ID NO: 7), CKACHMVQAPDGT-DIVK (SEQ ID NO: 8), GDVEKGKKIFIMKCSQCHTVE (SEQ ID NO: 9) or GDVEKGKKIFVQKCAQCHTVE (SEQ ID NO: 10). In yet other examples, the amino acid sequence of the peptide comprises any one of SEQ ID NOs: 4-10 with 1, 2, 3, 4 or 5 amino acid substitutions.

The porphyrin moiety of the microperoxidase comprises a metal ion. In some embodiments, the metal is a transition metal. In some examples, the transition metal is iron, zinc, palladium, manganese, cobalt, copper, nickel or cadmium. In one non-limiting example, the transition metal is iron. For example, in some instances, the metal iron is ferrous iron ($Fe^{2+}$).

In some embodiments, the porphyrin moiety comprises protoporphyrin IX. In some examples, protoporphyrin IX comprises an iron ion, such as $Fe^{2+}$. In other examples, iron is replaced with another transition metal, such as, but not limited to, zinc, palladium, manganese, cobalt, copper, nickel or cadmium.

In some instances, the amino acid composition of the peptide and/or the transition metal ion of the porphyrin moiety are selected to alter one or more properties of the microperoxidase. For example, modifications to the amino acid sequence and/or metal ion can be made to decrease peroxidase activity, to increase hydrophobicity or hydrophilicity (to increase plasma half-life or bioavailability), and/or to stabilize heme binding. In addition, particular amino acids may be selected in order to permit generation of a cyclic peptide.

In some embodiments, the method of removing carbon monoxide from hemoglobin in blood or tissue, or the method of reducing HbCO in blood or tissue, is an in vitro method.

In other embodiments, the method of removing carbon monoxide from hemoglobin in blood or tissue, or the method of reducing HbCO in blood or tissue, is an in vivo method, wherein contacting the blood or tissue with an isolated or recombinant microperoxidase comprises administering the isolated or recombinant microperoxidase to a subject.

In some embodiments, the subject has at least 3%, at least 5%, at least 10%, at least 15% or at least 20%, at least 30%, at least 40% or at least 50% carboxyhemoglobin (HbCO) in their blood prior to treatment.

In some embodiments, the isolated or recombinant microperoxidase is administered by intravenous infusion.

In some embodiments, the microperoxidase is administered to a subject at a dose of about 1 gram to about 300 grams, such as about 10 grams to about 100 grams, about 10 grams to about 50 grams, about 30 grams to about 300 grams, or about 30 grams to about 150 grams. In particular examples, the microperoxidase is administered to a subject at a dose of about 1, about 10, about 20, about 30, about 40, about 50, about 60, about 70, about 80, about 90, about 100, about 125, about 150, about 175, about 200, about 225, about 250 or about 300 grams.

The isolated or recombinant microperoxidase can be administered to a subject in a single dose, or in multiple doses as needed, to reduce HbCO to a non-toxic level.

In some embodiments, the dose administered to the subject is the amount of isolated or recombinant microperoxidase required to reduce HbCO by at least 1%, at least 2%, at least 3%, at least 4%, at least 5%, at least 10%, at least 15%, at least 20%, at least 25%, at least 30%, at least 40%, at least 50%, at least 60%, at least 70%, at least 80% or at least 90% (compared to the level of HbCO before treatment) in blood and/or tissue of the subject.

C. Production and Synthesis of Microperoxidases

Microperoxidases are comprised of a peptide covalently bound to a porphyrin moiety, such as heme, and can be derived from naturally occurring c-type cytochromes (Braun and Thöny-Meyer, *Proc Natl Acad Sci USA* 101(35):12830-12835, 2004). The peptide chain of a microperoxidase includes the motif CXXCH (SEQ ID NO: 1). The porphyrin moiety of the microperoxidase is covalently bound to the peptide via thioether links to the cysteine side chains (Spee et al., *Eur J Biochem* 241:215-220, 1996).

Microperoxidases can be generated by proteolytic digestion of c-type cytochromes. Methods of generating microperoxidases, such as MP6, MP8, MP9, MP11, MP17 and MP50, through proteolytic digestion have been previously described (see, e.g., Spee et al., *Eur J Biochem* 241:215-220, 1996; Rusvai et al., *Biochem Pharmacol* 37:4574-4577, 1988; Nakamura et al., *Tetrahedron Lett* 33:5409-5412, 1992; Adams et al., *Biometals* 7:214-220, 1994; Aron et al., *J Inorg Biochem* 27:227-243, 1986). MP6, MP8, MP9, MP11 and MP50, which have peptide chains of 6, 8, 9, 11 and 50 amino acids, respectively, have been derived from horse-heart cytochrome c; MP17 (with a 17 amino acid peptide) has been generated from cytochrome $c_{550}$ of *Thiobacillus versutus* (Spee et al., *Eur J Biochem* 241:215-220, 1996). The amino acid sequences of the MP6, MP8, MP9 and MP11 and MP17 peptides are set forth below:

MP6-
              (SEQ ID NO: 5)
CAQCHT MP8-
              (SEQ ID NO: 6)
CAQCHTVE -continued

MP9-
KCAQCHTVE
(SEQ ID NO: 7)

MP11-
VQKCAQCHTVE
(SEQ ID NO: 4)

MP17-
CKACHMVQAPDGTDIVK
(SEQ ID NO: 8)

The present disclosure also contemplates the use of alternative microperoxidase peptide sequences, such as the following:

GDVEKGKKIFIMKCSQCHTVE
(SEQ ID NO: 9)

GDVEKGKKIFVQKCAQCHTVE
(SEQ ID NO: 10)

SEQ ID NO: 9 and SEQ ID NO: 10 are derived from human and horse cytochrome c, respectively. These peptides have a longer N-terminal portion than the MP11 peptide of SEQ ID NO: 4. In some embodiments, SEQ ID NO: 9 and SEQ ID NO: 10 are produced in bacteria, such as *E. coli*.

Biosynthetic methods of generating recombinant microperoxidases have also been described (see Braun and Thöny-Meyer, *Proc Natl Acad Sci USA* 101(35):12830-12835, 2004). Braun and Thöny-Meyer describe a method for the in vivo synthesis of artificial microperoxidases by exploiting the secretion and cytochrome c maturation apparatuses of *Escherichia coli*.

In bacteria, c-type cytochromes are synthesized as precursor polypeptides with an N-terminal signal sequence for export to the periplasm by the general protein type II secretion system (Sec). After translocation, soluble c-type cytochromes are processed by leader peptidase (Thöny-Meyer and Künzler, *Eur J Biochem* 246:794-799, 1997). The covalent ligation of heme to the c-type cytochromes occurs on the periplasmic side of the cytoplasmic membrane. In *E. coli*, eight cytochrome c maturation proteins (CcmA-H) are required for this process (Thöny-Meyer et al., *J Bacteriol* 177:4321-4326, 1995; Grove et al., *Mol Microbiol* 19:467-481, 1996). In the system described by Braun and Thöny-Meyer, small peptides containing the CXXCH (SEQ ID NO: 1) motif are expressed in the *E. coli* periplasm, and a plasmid that constitutively expresses the ccmA-H operon is utilized to enable covalent attachment of heme, thereby providing a means to produce recombinant microperoxidases with alterations in the amino acid sequence of the peptide.

Microperoxidases, such as MP8, MP9 and MP11, are also commercially available, such as from Sigma-Aldrich (St. Louis, Mo.).

D. Methods of Testing the Effectiveness of an Isolated or Recombinant Microperoxidase Also provided herein are methods of testing the effectiveness of an isolated or recombinant microperoxidase for removing HbCO from blood or tissue (also referred to as scavenging CO from blood or tissue, for example RBC hemoglobin in blood or tissue). In some embodiments, the method includes contacting the isolated or recombinant microperoxidase with HbCO (such as contacting a sample comprising CO-saturated red blood cells) for a period of time sufficient to allow for transfer of CO to the microperoxidase, and measuring the change in HbCO over time and/or the change in deoxy-Hb over time. A decrease in HbCO over time and/or an increase in deoxy-Hb over time, indicates that the recombinant microperoxidase is effective in removing HbCO from blood or tissue. In some examples, the decrease in HbCO (and/or increase in deoxy-Hb) is about 10%, about 20%, about 30%, about 40%, about 50%, about 60%, about 70%, about 80% or about 90%.

In other embodiments, the method includes contacting the isolated or recombinant microperoxidase with HbCO (such as CO-saturated red blood cells) for a period of time sufficient to allow for transfer of CO to the microperoxidase (MP), and measuring the change in deoxy-MP and/or the change in CO-bound MP over time. A decrease in deoxy-MP over time and/or an increase in CO-bound MP over time, indicates that the recombinant microperoxidase is effective for removing HbCO from blood or tissue. In some examples, the decrease in deoxy-MP (and/or increase in CO-bound MP) is about 10%, about 20%, about 30%, about 40%, about 50%, about 60%, about 70%, about 80% or about 90%.

In some examples, the period of time sufficient to allow for transfer of CO to the microperoxidase is about 30 seconds, about one minute, about two minutes, about three minutes, about four minutes, about five minutes, about six minutes, about seven minutes, about 8 minutes, about nine minutes or about ten minutes. In some examples, the change in HbCO, deoxy-HB, deoxy-MP and/or CO-bound MP over time are measured by spectrophotometry, such as by detecting absorption changes in the microperoxidase spectrum following contacting the HbCO with the microperoxidase.

The following examples are provided to illustrate certain particular features and/or embodiments. These examples should not be construed to limit the disclosure to the particular features or embodiments described.

EXAMPLES

Example 1

Microperoxidase Removes CO from RBC Hemoglobin

A study was conducted to determine whether microperoxidases are capable of scavenging CO from red blood cells. The following protocol was followed:
1. Carbon monoxide-saturated red blood cells (RBC-CO) were combined with microperoxidase-11 (MP11) in the presence of 10 mM dithionite, to a final concentration of 50 µM hemoglobin A (HbA) and approximately 100 µM MP11.
2. A volume of 0.3 mL was removed and micro-centrifuged for five seconds.
3. The supernatant was removed and put into an empty micro-tube.
4. PBS with 10 mM dithionite and 0.5% NP40 was added to the RBC pellet.
5. Steps 2-4 were repeated until all of the reaction volume was depleted.
6. Absorbance of the RBCs in NP40/PBS, followed by absorbance of the supernatant samples (in the same order as centrifuged) was immediately measured.

Figure 1:
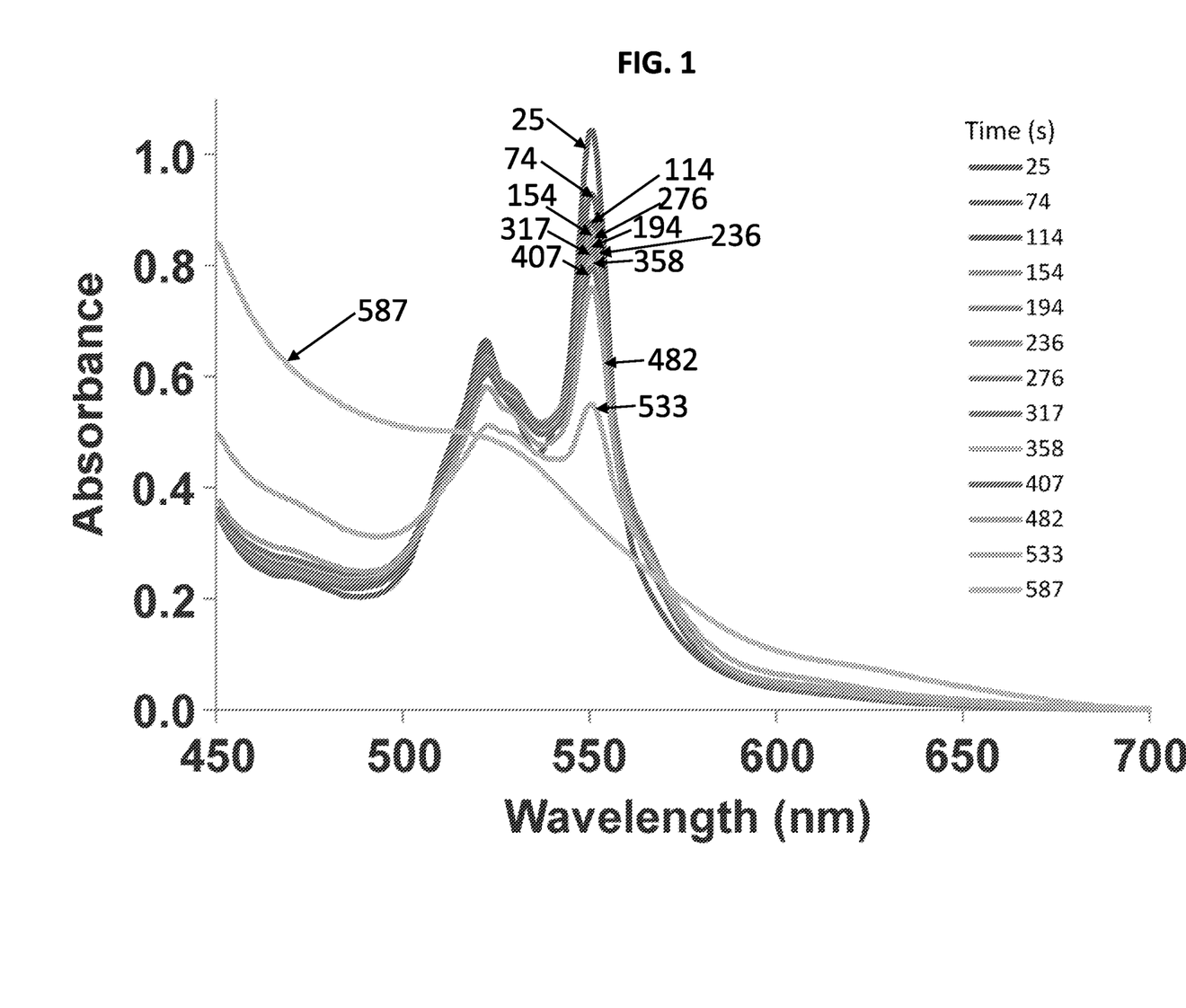
FIG. 1: Deoxy-MP11 scavenges CO from red blood cells (RBCs). The graph shows the absorption changes in the microperoxidase-11 (MP11) spectrum after mixing with CO-saturated red blood cells (RBC-CO). MP11 was mixed with RBC-CO and samples were extracted from the reaction mixture at different time points (25 to 587 seconds). MP11 was separated from the RBCs by centrifugation. The spectra indicate the decay of the deoxy-MP11 (peaks at 520 and 550 nm) to form CO-bound MP11.
Figure 2:
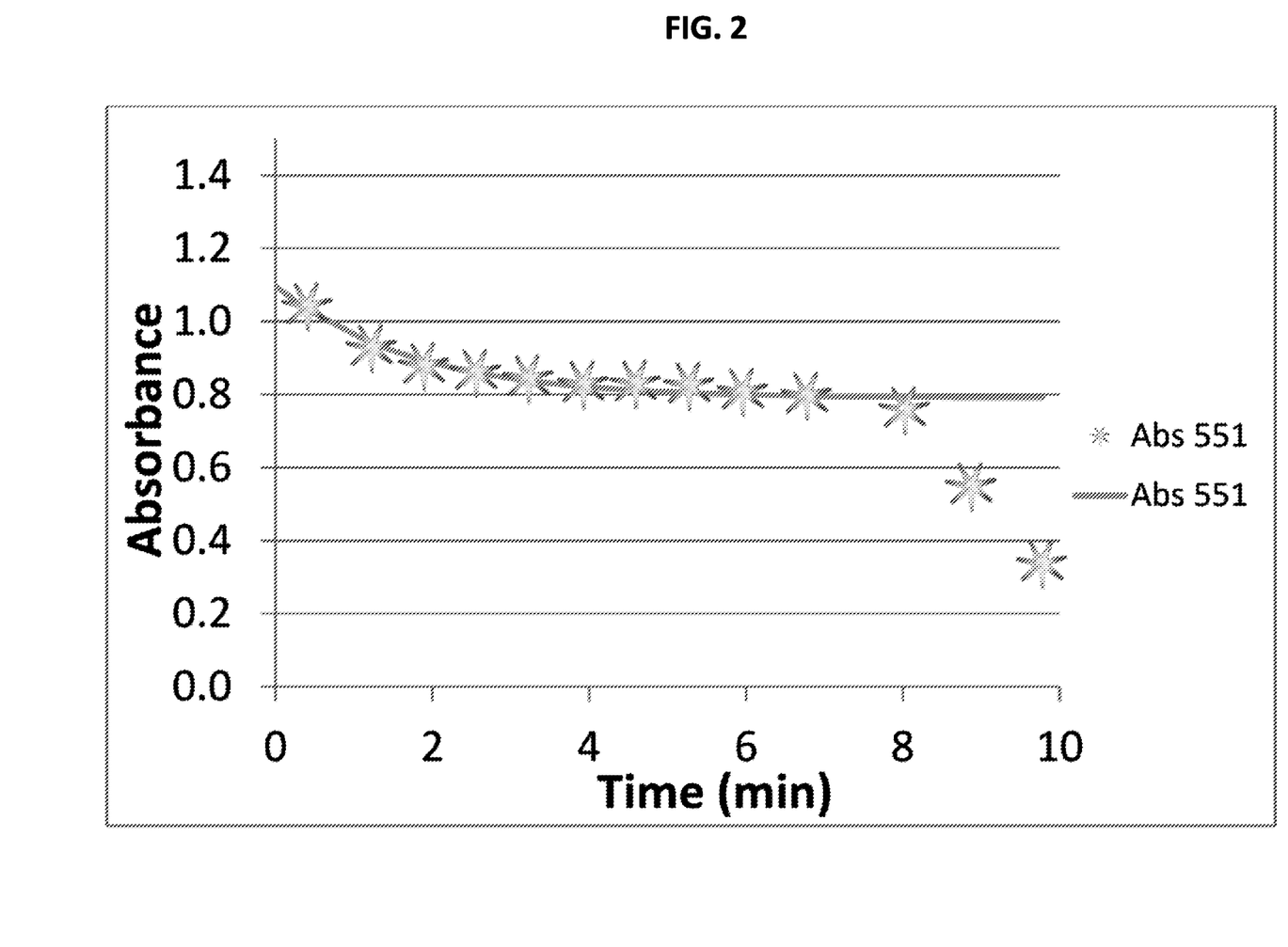
FIG. 2: Kinetics of MP11-mediated CO scavenging from RBCs. The rate of CO binding to MP11 was monitored following the decay of absorbance at 551nm. Each data point (*) represents a selected timepoint measurement; the solid line denotes a single exponential decay fit.
Figure 3:
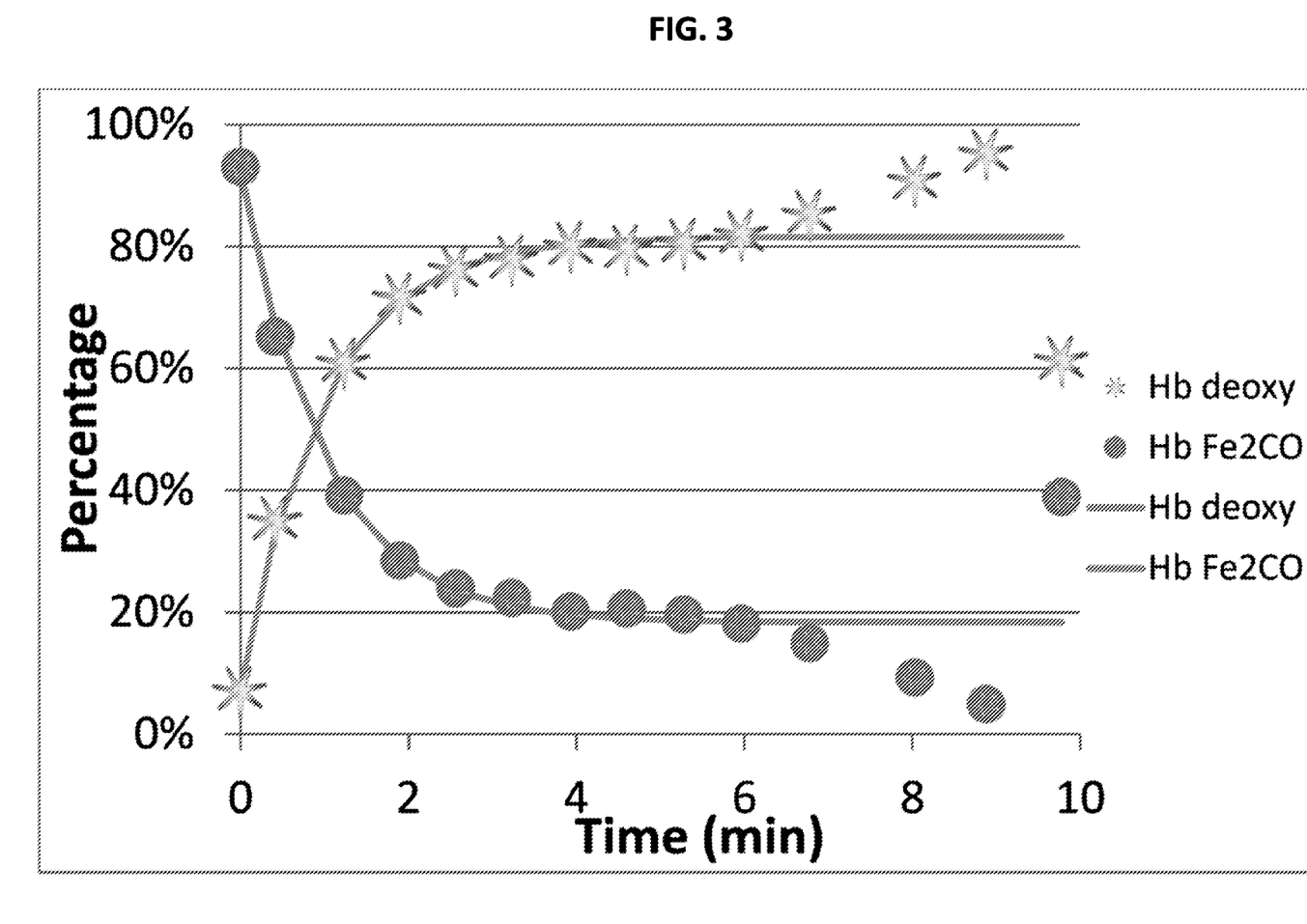
FIG. 3: Mixing of CO-saturated red blood cells with MP11 results in net transfer of CO from hemoglobin to MP11. The data points indicate the relative amount of CO-bound (circle) or deoxy (*) hemoglobin at selected time points after mixing. The solid lines denote a fit to a single exponential equation.

The absorption changes in the MP11 spectrum following mixing with RBC-CO are shown in FIG. 1. The spectra indicate decay of deoxy-MP11 to form CO-bound MP11. The rate of CO binding to MP11 was monitored following the decay of absorbance at 551 nm. The kinetics of MP11-medated CO scavenging from RBCs is shown in FIG. 2. The change in hemoglobin species at selected timepoints (0, 2, 4, 6, 8 and 10 minutes) after mixing with deoxy-MP11 is shown in FIG. 3. As evidenced by the increase in deoxy-Hb (and the corresponding decrease in HbCO) over time, the mixing of CO-saturated red blood cells with MP11 resulted in a net transfer of CO from hemoglobin to MP11. Thus, these results demonstrate that MP11 scavenges CO from RBC hemoglobin.

Example 2

Method of Treating a Subject with an Isolated or Recombinant Microperoxidase

This example describes the use of an isolated or recombinant microperoxidase for the treatment of a human subject with carboxyhemoglobinemia (or CO poisoning).

A subject diagnosed with or suspected of having carboxyhemoglobinemia is selected for treatment. A therapeutically effective amount of an isolated or recombinant microperoxidase is administered to the subject, such as by intravenous infusion. In some examples, the microperoxidase is MP11 and the human subject is administered 10-100 grams of MP11. In other examples, the microperoxidase is a recombinant microperoxidase and the human subject is administered 30-300 grams of the recombinant microperoxidase. A medical practitioner can determine an appropriate therapeutic dose and adjust the dose as needed to effectively decrease HbCO in the subject. The levels of HbCO can be measured in the subject to determine that an effective dose has been administered. Additional doses can be provided if needed in order to decrease HbCO to an acceptable level (such as ≤5% for a smoker or ≤15% for a smoker).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating carboxyhemoglobinemia in a subject by selecting a subject with carboxyhemoglobinemia and administering to the subject, via intravenous injection or infusion, a therapeutically effective amount of a pharmaceutical composition consisting of a pharmaceutically acceptable carrier and an isolated or recombinant microperoxidase, wherein the isolated or recombinant microperoxidase consists of a peptide covalently bound to a porphyrin moiety, and wherein the amino acid sequence of the peptide comprises any one of SEQ ID NOs: 4-10.

2. The method of claim 1, wherein the amino acid sequence of the peptide consists of any one of SEQ ID NOs: 4-10.

3. The method of claim 1, wherein the porphyrin moiety comprises a metal ion.

4. The method of claim 3, wherein the metal is iron, zinc, palladium, manganese, cobalt, copper, nickel or cadmium.

5. The method of claim 1, wherein the porphyrin moiety comprises protoporphyrin IX.

6. The method of claim 5, wherein the porphyrin moiety further comprises iron.

7. The method of claim 1, wherein the subject has at least 5%, at least 10%, at least 15%, at least 20%, at least 30%, at least 40% or at least 50% carboxyhemoglobin in blood relative to total hemoglobin.

8. The method of claim 1, wherein the isolated or recombinant microperoxidase is administered by intravenous infusion.

9. The method of claim 1, wherein the isolated or recombinant microperoxidase is administered in an amount required to decrease carboxyhemoglobin (HbCO) by at least 1% to at least 90% in blood or tissue of the subject.

10. The method of claim 9, wherein the isolated or recombinant microperoxidase is administered in an amount required to decrease HbCO by at least 20% in blood or tissue of the subject.

11. The method of claim 9, wherein the isolated or recombinant microperoxidase is administered in an amount required to decrease HbCO by at least 50% in blood or tissue of the subject.

* * * * *